(12) United States Patent
Stratton et al.

(10) Patent No.: US 6,258,532 B1
(45) Date of Patent: Jul. 10, 2001

(54) METHODS FOR IN VITRO SUSCEPTIBILITY TESTING OF CHLAMYDIA

(75) Inventors: Charles W. Stratton; William M. Mitchell, both of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/025,176

(22) Filed: Feb. 18, 1998

Related U.S. Application Data

(63) Continuation-in-part of application No. 08/911,593, filed on Aug. 14, 1997, now abandoned.

(51) Int. Cl.$^7$ .............................. C12Q 1/68; C12Q 1/37; C12Q 1/18; G01N 33/571; C12P 19/34
(52) U.S. Cl. ............................. 435/6; 435/7.36; 435/23; 435/32; 435/34; 435/91.2; 536/23.7
(58) Field of Search ................................ 435/6, 7.36, 32, 435/91.2, 23, 34; 536/23.7, 24.32, 24.33

(56) References Cited

U.S. PATENT DOCUMENTS

| | | | |
|---|---|---|---|
| 3,996,355 | 12/1976 | Linn et al. | 424/228 |
| 5,217,493 | 6/1993 | Raad et al. | 623/11 |
| 5,650,405 | 7/1997 | Remington et al. | 514/183 |
| 5,795,563 | 8/1998 | Kallick et al. | 424/9.361 |
| 5,800,989 * | 9/1998 | Linn et al. | 435/6 |
| 5,869,608 | 2/1999 | Caldwell et al. | 530/350 |
| 6,043,225 | 3/2000 | Shor et al. | 514/29 |

FOREIGN PATENT DOCUMENTS

| | | |
|---|---|---|
| 1 156 589 | 8/1997 | (CN) . |
| 1 190 581 | 8/1998 | (CN) . |
| 0439330 A2 | 1/1991 | (EP) . |
| 0699688 A2 | 3/1996 | (EP) . |
| 2 134 292 | 12/1972 | (FR) . |
| WO 98 06435 | 2/1998 | (WO) . |
| WO 98 10789 | 3/1998 | (WO) . |
| WO 98 50074 | 11/1998 | (WO) . |
| WO 00 01378 | 1/2000 | (WO) . |

OTHER PUBLICATIONS

Everett, K.D. et al. J. Bacteriol. 177(4):877–882, Feb. 1995.*
Bertrand et al., "L'Ofloxacine (RU 43280) etude clinique" *Path Biol.* 35:629–633 (1987) abstract only.
Drancourt et al., "Oral rifampin plus ofloxacin for treatment of staphylococcus–infected orthopedic implants" *Antimicrobial Agents and Chemotherapy* 37:1214–1218 (199f3).
Freidank et al., "In vitro susceptibilities of *Chlamydia pneumoniae* isolates from german patients and synergistic activity of antibiotic combinations" *Antimicrobial Agents and Chemotherapy* 43:1808–1810 (1999).
Lay–Schmitt et al., "Evidence for infection with *Chlamydia pneumoniae* in subgroup of patients with multiple sclerosis" *Annals of Neurology* 47:652–655 (2000).
Sriram et al., "Multiple sclerosis associated with *Chlamydia pneumoniae* infection of the CNS" *Neurology* 50:571–572 (1998).
Sriram et al., "*C. pneumoniae* infection of the CNS in patients with relapsing remitting MS" *Neurology* 52:A558 (1999).
Sriram et al., "*Chlamydia pneumoniae* infection of the central nervous system in multiple sclerosis" *Annals of Neurology* 46:6–14(1999).
Yao et al., "Association between *C. pneumoniae* and MS," *Journal of Neuroimmunology* 90:70 (1998).
Yao et al., "CNS infection with *C. pneumoniae* in MS," *Neurology* 50:A423–A424 (1998).
Yao et al., "Reactivity of oligoclonal bands seen in CSF to *C. pneumoniae* antigens in patients with Multiple Sclerosis," *Neurology* 52:A559 (1999).
Coles, A.M. et al. FEMS Microbiology Letters 106:193–200, 1993.*
Khan, M.A. et al. J. Antimicrobial Chemotherapy 37:677–685, Apr. 1996.*
Beatty, W.L. et al. Microbiological Reviews 58(4):686–699, Dec. 1994.*
Neeper, I.D. et al. Infection and Immunity 58(7):2042–2047, Jul. 1990.*
Gaydos, C.A. et al. Clinical Infectious Diseases 17:718–23, 1993.*
Hackstadt, T. et al. J. Bacteriology 161(1):25–31, Jan. 1985.*
Tjhie, H.T.J. et al. J. Microbiological Methods 18:137–150, 1993.*
Kaltenboeck, B. et al. J. Bacteriology 175(2):487–502, Jan. 1993.*
Carter, M.W. et al. J. General Microbiology 137:465–475, 1991.*
Hammerschlag, M.R. et al. Clinical Infectious Diseases 14:178–182, 1992.*
Heinonen, Pentti K., et al., "A Comparison of Ciprofloxacin with Doxycycline plus Metronidazole in the Treatment of Acute Pelvic Inflammatory Disease", Scand. J. Infect. Dis. Suppl., 60: 66–73 (1989).
Burchell, H.J., et al., "Efficacy of Different Antibiotics in the Treatment of Pelvic Inflammatory Disease", *SAMJ.*, 72: 248–249 (Aug. 15, 1987).

(List continued on next page.)

*Primary Examiner*—Carla J. Myers
*Assistant Examiner*—Diana Johannsen
(74) *Attorney, Agent, or Firm*—Clark & Elbing LLP

(57) ABSTRACT

Methods for determining the susceptibility of intracellular pathogens, particularly Chlamydia, to single or combination of test agents are described. The methods can be used for in vitro or in vivo evaluation of agents that can be used as therapeutic agents in the treatment/eradication of pathogen infection in general or to target a specific infected organ. Assays which utilize nucleic amplification techniques (e.g., PCR) to determine effectiveness of the agent(s) evaluated are also described.

17 Claims, No Drawings

OTHER PUBLICATIONS

Paavonen, J., et al., "Factors Predicting Abnormal Hysterosal–pingographic Findings in Patients Treated for Acute Pelvic Inflammatory Disease", *Int. J. Gynaecol. Obstet.*, 23: 171–175 (1985).

Miettinen, A., et al., "The Effect of Ciprofloxacin and Doxycycline Plus Metronidazole on Lower Genital Tract Flora in Patients with Proven Pelvic Inflammatory Disease", *Arch. Gynecol. Obstet.*, 249: 95–101 (1991).

Judlin, P., et al., "Etude Comparative Des Associations Ofloxacine + Amoxicilline–Acide Clavulanique Versus Doxycycline + Amoxicilline–Acide Clavulanique Dans Le Traitement Des Infections Génitales Hautes A *Chlamydia Trachomatis*", *J. Gynecol. Obstet. Biol. Reprod.*, 24: 253–259 (1995).

Henry–Suchet, J., "Traitement Des Infections Utéro–Annexielles Sexuellement Transmises (IUAST) Sauf Syphilis Et Herpés", Méd. Mal. Infect., 24: 379–387 (1994).

Joly–Guillou, M.L., et al., "Bactéries Isolées En 1994–1995 Au Cours Des Infections Gynécologiques Hautes Et Des Uréthrites Masculines", *La Presse Médicale* 2–9 Mars 25, (8): 342–348 (1996).

Orfila, J. and Haider, F., "Comparative Study Of The In Vitro Activity Of Lomefloxacin Versus Lomefloxacin Combined With Metronidazole Versus Lomefloxacin In Combination With Amoxicillin/Clavulanic Acid Against *Chlamydia Trachmatis*", Intern. J. Antimicro. Agents, 2: 11–14 (1992).

Witte, E.H., et al., "A Comparison Of Pefloxacin/Metronidazole And Doxycycline/Metronidazole in the Treatment of Laparoscopically Confirmed Acute Pelvic Inflammatory Disease", *Eur. J. Obstet. Gynec. and Repro. Bio.*, 50: 153–158 (1993).

* cited by examiner

METHODS FOR IN VITRO SUSCEPTIBILITY TESTING OF CHLAMYDIA

RELATED APPLICATION

This application is a continuation-in-part application of U.S. Ser. No. 08/911,593 filed Aug. 14, 1997 (now abandoned), hereby incorporated by reference.

BACKGROUND OF THE INVENTION

It has long been recognized that the appropriate use of susceptibility testing allows the most effective use of antimicrobial agents for the therapy of infectious diseases (1,2). Susceptibility testing for microorganisms such as the chlamydiae that cannot be cultured without the use of animal or tissue cultures is well recognized as being quite difficult (3,4). Early work used embryonated egg yolk sacs, and animal models, but these techniques were slow and cumbersome (5). In vitro susceptibility testing of chlamydiae is currently done using tissue culture cell lines (3–10). In these cell culture procedures, cycloheximide or a similar agent is routinely used to impair host cell metabolism and thus provide intracellular conditions in the host cell that enhance chlamydial growth. The use of cycloheximide has been found to increase the size and visibility of the chlamydial inclusion bodies. After a period of incubation, visual detection of inclusion bodies or immunochemical detection of chlamydial antigen is the endpoint (3,4). The minimal inhibitory concentration (MIC) is generally defined as the lowest concentration of antimicrobial agent at which no inclusion is seen after incubation. The minimal chlamydiacidal concentration (MCC) is defined as the lowest concentration of antimicrobial agent at which no inclusion is seen after several passages.

The murine model has been used extensively for the in vivo evaluation of chlamydial infection (11–18). Therefore, it is not surprising that in addition to in vitro cell culture methods, the murine model of chlamydial infection is also used for in vivo susceptibility testing (17).

Susceptibility testing of chlamydiae, including the most recent species C. pneumoniae, has been relatively extensive considering the difficulties encountered in testing an intracellular microorganism (3,5,10,19–21), and the results are considered to be consistent (5). However, in vitro susceptibility testing methods for chlamydiae are not standardized in terms of the testing conditions (3,4). Standardization of testing conditions for susceptibility testing is a well recognized requirement in general (1,2) and likewise should be required for chlamydiae (3). Moreover, results from in vitro susceptibility testing methods using current tissue culture conditions may not reflect the results seen with in vivo conditions (1–3). For example, Wyrick et al. (22) has shown that susceptibility testing results were different with polarized human endothelial cells as opposed to nonpolarized cells. Other conditions of testing have been found to markedly influence the results of chlamydial susceptibility testing (17). The timing of the addition of the antimicrobial agents to the cell culture is particularly important: the addition of agents before infection of the cell culture may lower the MICs and MCCs by 8-fold (23). Accordingly, the antimicrobial agents are usually added 30 to 60 minutes after the cells are infected (3,4).

Another common difficulty is determining the endpoint of the susceptibility test. This is a critical issue in both in vitro and in vivo methods (1–3). Visualization of the inclusion body by fluorescent microscopy is usually done (4) and is known to be observer-dependent (3). Attempts at achieving a more accurate and less subjective endpoint have been made. Kahn and colleagues (24) have recently reported a reverse transcriptase-PCR based assay for in vitro susceptibility testing of Chlamydia pneumoniae which avoids many of the problems associated with the determination of the endpoint. This method uses Southern hybridization to detect PCR-amplified messenger RNA. These investigators found that the use of this test method resulted in higher MICs and MCCs for a test strain as compared to results with conventional methods. It should be noted, however, that since messenger RNA is only present in active, metabolizing bacteria, this endpoint only indicates the presence or absence of active bacteria.

Another potential problem with current susceptiblity testing methods is the routine use of cycloheximide. The effect of antimicrobial agents against metabolizing chlamydiae requires that the agent penetrate the infected cell. The physiochemical properties of drugs are the main factors that influence their distribution in tissues and penetration in cells. However, the penetration of antimicrobial agents into the host cells can be greatly influenced by energy-requiring mechanisms such as active transport of the agent into the host cell or active efflux of the agent out of the host cell. The use of cycloheximide negates such mechanisms in the host cell. The measurement of antimicrobial levels in cells is a recognized problem and needs additional research (25). Until such work is done, the potential influence of cycloheximide on the penetration of antimcrobial agents is probably best avoided by selecting a different endpoint in which visualization of the inclusion body is not used.

The murine model for the therapy for chlamydial infections has been used more frequently in an attempt to avoid some of the problems encountered with in vitro susceptibility test methods. One group of investigators have demonstrated discrepancies between the in vitro MICs and survival rates (26,27). This data suggests that an in vivo animal model is more predictive of clinical outcome than is the current cell culture system. Unfortunately, the end point of such animal studies is still a problem. Although survival is a clearly discernible endpoint, it does not address the issue of cryptic infections which may be present in the survivors. If antimicrobial therapy can induce cryptic chlamydial infection, and cryptic infection then causes chronic diseases such as atherosclerosis, a method for detecting cryptic infection in animal models is needed.

SUMMARY OF THE INVENTION

The invention pertains to in vitro and in vivo susceptibility tests for identifying agent(s) capable of significantly reducing/eliminating infection caused by intracellular pathogens, such as Chlamydia and particularly Chlamydia pneumoniae. The methods comprise preparing tissue culture from cell lines; inoculating these cells with intracellular pathogen (e.g., Chlamydia) in the absence of cycloheximide; allowing the pathogen to infect these cells for several days; adding agent(s) to be tested, which agent(s) is/are replaced as needed for the duration of incubation; isolating pathogen nucleic acid from the cells; and assessing the presence or absence of pathogen DNA using a suitable nucleotide amplification assay, such as PCR. Preferably the presence or absence of signal for amplified DNA encoding a protein of the intracellular pathogen is determined. In one embodiment, the presence or absence of DNA encoding MOMP of Chlamydia or other chlamydial protein is determined. Absence of a signal indicates a reduction in the degree of infection below that which is detectable by nucleic acid amplification techniques and strongly suggests eradication of the microorganism. The susceptibility tests described herein are particularly useful as a drug screening tool for assessing the activity of single agents or combinations of agents against intracellular pathogen infection.

The invention is described below with regard to Chlamydia species and *Chlamydia pneumoniae* in particular as illustrative of the intracellular pathogen. However, it should be understood that other intracellular pathogens are embraced by this invention.

The unique and novel aspect of the susceptabilty test described here within is that it measures the presence or absence of chlamydial DNA and thus can detect cryptic forms and/or elementary bodies both of which are infectious, yet are not replicating.

DETAILED DESCRIPTION OF THE INVENTION

This invention pertains to novel approaches for the susceptibility testing of Chlamydia species that are necessitated by the complex life cycle of the chlamydial pathogen as well as by its diverse, extensive, and heretofore unappreciated ability to cause chronic, cryptic, and persistent systemic infections that are refractory to short duration therapy with conventional single agents. The inventors have discovered that successful eradication of chronic/systemic chlamydial infections can be predicted by using the described unique methods for in vitro and in vivo susceptibility testing.

The invention is based upon the discovery that current susceptibility testing methods for Chlamydiae do not accurately predict the ability of antimicrobial agents to successfully and totally eradicate chronic chlamydial infections. This is because the current susceptibility testing methods measure only replication of chlamydia and ignores the well-known "cryptic phase" (28–33) in which Chlamydiae are not actively replicating. Moreover, it has also been discovered that the so-called "cryptic phase" of Chlamydiae includes multiple and different phases. The following are phases of the chlamydial life cycle in which the Chlamydiae are not replicating: an initial intranuclear phase in which elementary bodies (EBs) transition to reticulate bodies (RBs), an intracytoplasmic phase in which there is a transition of the RB phenotype to the EB phenotype, an intracytoplasmic phase with a nonreplicating, but metabolizing RB, and intracellular/extracellular EB phases in which there is neither replication nor metabolsim. In order to assess the cumulative and long term effect of antimicrobial therapy on these multiple life phases, unique in vitro and in vivo susceptibility test methods have been developed and are described herein.

The term "susceptibility" as used herein is intended to mean a physiological response of an organism to an environmental or chemical stimuli. The desired physiological response to stimuli is one which adversely affects the pathogen's viability to replicate or reside within the host cell and, ideally, would result in the complete elimination (i.e., death) of that pathogen.

In Vitro Methodology

One aspect of the invention pertains to methods for evaluating the susceptibility of the distinct phases and stages of the life cycle of Chlamydia, to a particular agent(s), particularly the cryptic phase, since prior techniques have failed, heretofore, to appreciate the need for drugs that can clear infected cells of cryptic Chlamydia. A preferred drug screening method which accomplished this objective utilizes tissue culture cells, in the absence of cycloheximide in order to encourage cryptic infection. Cryptic infection is less likely to occur in cells used in standard cell culture susceptibility techniques because Chlamydia in cycloheximide-paralyzed cells need not compete with the host cell for metabolites and hence are encouraged to replicate.

In a preferred embodiment, the cells are grown in a culture medium in which chlamydial forms have been inactivated as described in U.S. Ser. No. 09/025,174 entitled "Chlamydia-Free Cell Lines and Animals", filed concurrently herewith; the entire teachings of which are incorporated herein by reference.

The in vitro method uses standard tissue culture cells, but without the addition of cycloheximide. Moreover, the chlamydiae are allowed to replicate for several days prior to the addition of at least one test agents. A "test agent" can be any compound to be evaluated as an antichlamydial agent for its ability to significantly reduce the presence of Chlamydia in living cells. For example, a test agent can include, but is not limited to, antibiotics, antimicrobial agents, antiparasitic agents, antimalarial agent, disulfide reducing agents and antimycobacterial agents. The test agent(s) is/are replaced when needed for the duration of the incubation time (days to weeks) to ensure that the test agent is present and has not been otherwise degraded. Antimicrobial agent(s) (test agent) is then added to the replicating cells. The antimicrobial agents/growth medium are periodically replaced for the duration of the incubation time, which is preferably weeks rather than days. Finally, the end point after the prolonged incubation time is the complete absence of chlamydial DNA, as determined by a nucleic acid amplification technique, such as the polymerase chain reaction (PCR) methodology. Standard nucleic acid amplification techniques (such as PCR) are used to ascertain the presence or absence of signal for chlamydial DNA encoding MOMP or other unique Chlamydia protein to determine whether the test agent or combination of agents is/are effective in reducing Chlamydia infection. The loss of signal (i.e., below the detectable level of the nucleic acid amplification technique) in cells with antibiotic(s) versus its presence in controls is an indication of efficacy of the agent or combination of agents against Chlamydia.

Accordingly, the susceptibility test of this invention can be used to identify an agent or agents which are effective against any particular species of Chlamydia and can be used to identify agent(s) effective against the cryptic form of the pathogen, i.e., is capable of inhibiting or eliminating the cryptic form of the pathogen. Agents that are effective against Chlamydia, as ascertained by the susceptibility testing protocols described herein, can be used as part of a therapy for the management of Chlamydia infections. Suitable therapeutic protocols are described in detail below, with a particular focus on targeting agents toward specific stages of the chlamydial life cycle.

The methods described herein are unique because they evaluate the activity of antimicrobial agents in the absence of cycloheximide which provides a more clinically relevant intracellular milieu. For example, any energy-dependent host cell membrane pumps which might move antimicrobial agents in or out of the cell are inactivated by the use of cycloheximide. The methods described herein are unique because they utilize culture medium which has previously been inactivated. The methods are also unique because they measure the effect of a prolonged duration of exposure to the antimicrobial agent(s) after the intracellular infection by chlamydiae has become established. Finally, the method is unique because it measures the presence/absence of chlamydial DNA as the endpoint, for example by measuring PCR signal. By using complete eradication of chlamydial DNA as an endpoint, the susceptibility test confirms that all phases of Chlamydiae have been eradicated as opposed to merely a temporary halt in replication.

When PCR is the preferred methodology used to evaluate assay endpoint, the PCR method can be enhanced by the unique application of a reducing agent, such as dithiothreitol (DTT), in order to uncoat chlamydial EBs and hence allow exposure of the DNA. In other words, DTT permits the EB coating to rupture. By using an assay for DNA in which EBs are specifically uncoated, the susceptibility test endpoint assesses the presence or absence of EBs as well as the presence or absence of both replicating and nonreplicating RBs. Thus, this approach for chlamydial susceptibility testing allows quantitative antimicrobial susceptibility assays of single and combination agents in which the cumulative effect of the agent(s) on the complete eradication of all life phases is measured. Examples of results obtained with this in vitro method are described below.

In one embodiment, a suitable nucleic acid assay for identifying agents effective against the cryptic form of chlamydia comprises, in the presence of agent(s) to be tested, subjecting cultured cells to protease/reducing agent (e.g., dithioreitol) and protease digestion or guanidine isothiocyanate (also known as guanidine thiocyanate) for a prescribed period of time; extracting DNA from the treated solution; exposing DNA to appropriate polymerase, dNTPs and primers for DNA amplification of MOMP or other protein of the Chlamydia species; and determining the presence or absence of amplified DNA by visualizing the ethidium bromide treated DNA product by gel electrophoresis, for example. In particular embodiments, the Chlamydia species is *C. pneumoniae* and the appropriate primers are ATG AAA AAA CTC TTA AAG TCG GCG TTA TTA TCC GCC GC (SEQ ID NO: 1), hereafter CHLMOMPDB2 and TTA GAA TCT GAA CTG ACC AGA TAC GTG AGC AGC TCT CTC G (SEQ ID NO: 1), hereafter CHLMOMPCB2.

The invention further relates to a method of identifying cells containing the cryptic form of a Chlamydia species by a nucleic acid amplification technique (e.g., PCR) comprising subjecting cultured cells to protease digestion; stopping protease activity; exposing cells to appropriate heat-stable DNA polymerase, dNTPs and labeled primers (e.g., 3'-biotin labeled, 5'-biotin labeled) for amplification of DNA encoding MOMP of the Chlamydia species; washing the cells; exposing the cells to a reporter molecule (e.g., strepavidin-conjugated signal enzyme); exposing the cells to an appropriate substrate for the reporter molecule (e.g., conjugated enzyme); and visualizing the amplified DNA encoding MOMP by visualizing the product of the reaction.

The invention pertains to a method of identifying cells containing the cryptic form of Chlamydia. The method comprises treating cultured cells, thought to be infected with Chlamydia, with a disulfide reducing agent; subjecting cultured cells to protease digestion; exposing cells to appropriate polymerase, dNTPs and primers for DNA amplification of nucleic acid encoding of a chlamydial protein; exposing the cells to a reporter molecule enzyme; exposing the cells to an appropriate substrate for the reporter enzyme; and determining the presence of the cryptic form of Chlamydia by visualizing the amplified DNA encoding a chlamydial protein. Preferably the amplification technique is PCR and the primers are CHLMOMPDB2 and CHLMOMPCB2 of *Chlamydia pneumoniae*.

A similar method can be used as an assay for identifying an agent which is effective against the cryptic form of Chlamydia. Accordingly, the method comprises treating cultured cells grown in the absence of cycloheximide, thought to be infected with Chlamydia, with a disulfide reducing agent; allowing the Chlamydia to replicate; adding a test agent; subjecting cultured cells to protease digestion; exposing cells to appropriate polymerase, dNTPs and primers for DNA amplification of a gene encoding chlamydial protein; exposing the cells to a reporter molecule enzyme; exposing the cells to an appropriate substrate for the reporter enzyme; and determining the presence of cryptic form of Chlamydia by visualizing the amplified DNA encoding a chlamydial protein, such as MOMP.

A detailed description of primers, PCR techniques and other methodologies useful for the present invention are provided in U.S. patent application Ser. No. 08/911,593, filed Aug. 14, 1997, entitled "Diagnosis and Management of Infection Caused by Chlamydia" by William M. Mitchell and Charles W. Stratton; U.S. patent application Ser. No. 09/025,174 entitled "Chlamydia Free Cell Lines Animals" (Attorney's Docket No. VDB98-03), filed concurrently herewith; and U.S. patent application Ser. No. 09/025,596 entitled "Identification of Antigenic Peptide Sequences" (Attorney Docket No. VDB98-01), filed concurrently herewith; the entire teaching of these applications are incorporated herein by reference.

In Vitro Susceptibility Testing Results.

Two week exposure of single agents including the fluoroquinolone, ofloxacin, and the macrolide, clarithromycin, at 1 $\mu$g/ml failed to clear HeLa cells in culture of a detectable PCR signal for the MOMP gene of *Chlamydia pneumoniae*. In contrast, triple agents consisting of isoniazid (INH), metronidazole, and penicillamine (1 $\mu$g/ml each) resulted in no detectable PCR signal (Table 1). None of these agents, effective in the triple combination, is currently recognized as an anti-chlamydial agent.

Table 2 provides the results of an expanded study of antimicrobial susceptibilities at two different concentrations of antimicrobial agents, used alone and in combination, when exposed to the antimicrobial agents for two weeks. In addition to the agents already mentioned, minocycline, doxycycline, rifampin and sulfamethoxizole/trimethoprim, at all concentrations tested, failed to clear the PCR signal for chlamydial MOMP. Only the triple combination of isoniazid, metronidazole and penicillamine cleared the PCR signal. The triple combination was effective at both low and high concentrations. Table 2 also demonstrates the effect of a 4 week exposure with the same expanded series of antimicrobial agents alone and in combination. A number of triple combinations of antimicrobial agents resulted in cell cultures in which the PCR signal for the chlamydial MOMP gene could not be detected.

TABLE 1

Susceptibility to Antibiotics for Cryptic
*Chlamydia pneumoniae* Cultured in HeLa Cells[a]

| Antibiotic | Conc ($\mu$g/ml) | PCR[b] |
|---|---|---|
| Ofloxacin | 1 | positive |
| Clarithromycin | 1 | positive |
| INH | 1 | positive |
| Metronidazole | 1 | positive |
| Penicillamine | 1/1 | positive |

TABLE 1-continued

Susceptibility to Antibiotics for Cryptic
*Chlamydia pneumoniae* Cultured in HeLa Cells[a]

| Antibiotic | Conc (μg/ml) | PCR[b] |
|---|---|---|
| INH + Metronidazole + Penicillamine | 1/1/4 | negative |
| Control | 0 | positive |

[a]Cultured in the presence of the indicated antibiotic(s), but with no cycloheximide. Media changes at 48–72 hours.
[b]Analysis following 2 week exposure to antimicrobial agents.

TABLE 2

Susceptibility to Antibiotics for Cryptic
*Chlamydia pneumoniae* Cultured in HeLa Cells[a] by PCR

| Antibiotic | Conc (μg/ml) | PCR 2 week | PCR 4 week |
|---|---|---|---|
| Minocycline | 1 | pos | pos |
| Doxycycline | 1 | pos | pos |
| Isoniazide | 1 | pos | pos |
| TMP/SMZ[b] | 100 | pos | pos |
| Minocycline + Metronidazole + penicillamine | 1/1/4 | pos | pos |
| Doxycyclin + Metronidazole + penicillamine | 1/1/4 | pos | neg |
| Isoniazid + Metronidazole + penicillamine | 1/1/4 | neg | neg |
| TMP/SMZ + Metronidazole + penicillamine | 100/1/4 | pos | neg |
| Metronidazole | 0.25 | pos | pos |
| Clarithromycin | 0.25 | pos | pos |
| Rifampin | 0.25 | pos | pos |
| Ofloxacin | 0.25 | pos | pos |
| Minocycline | 0.25 | pos | pos |
| Doxycycline | 0.25 | pos | pos |
| TMP/SMZ + Metronidazole | 25/0.25 | pos | |
| Ofloxacin + Metronidazole | 0.25/0.25 | pos | pos |
| Rifampin + Metronidazole + penicillamine | 0.25/0.25/4 | pos | pos |
| Rifampin + Metronidazole + Ofloxacin | 0.25/0.25/0.25 | pos | pos |
| Clarithromycin + Metronidazole + penicillamine | 0.25/0.25/1 | pos | neg |
| Doxycycline + Metronidazole + penicillamine | 0.25/0.25/1 | pos | pos |
| Minocycline + Metronidazole + penicillamine | 0.25/0.25/1 | pos | neg |
| Isoniazid + Metronidazole + penicillamine | 0.25/0.25/1 | neg | neg |
| TMP/SMZ | 0.25 | | pos |
| Rifampin + Metronidazole | 0.25/0.25 | | pos |
| None | 0 | pos | pos |

[a]Cultured in the presence of the indicated antibiotics, but with no cycloheximide. Media changes at 48–72 hours. pos = positive; neg = negative
[b]TMP/SMZ = trimethoprim/sulfamethoxazole

In Vivo Methodology

In another aspect of the invention, the susceptibility test can be used to evaluate the status of a human or animal undergoing therapy for the management of Chlamydia infection. For example, a biological material is isolated from the human or animal undergoing combination therapy. The biological material is treated such that the Chlamydia is isolated therefrom. This chlamydial isolate is allowed to infect Chlamydia free cells. These infected cells are then exposed to the combination of agents being used in the individual undergoing combination therapy. Alternatively, the individual's serum containing the antimicrobial agents can be added to the infected cells as a "serum bactericidal test" for intracellular chlamydial infection. Methods for producing Chlamydia free cells are described in U.S. patent application Ser. No. 09/025,174, entitled "Chlamydia Free Cell Lines and Animals" (Attorney's Docket No. VDB98-03), filed concurrently herewith; the entire teachings of which are incorporated herein by reference.

The in vivo method uses the murine model although other animals such as rats or rabbits can be used. In this method, mice (or any other animal) are inoculated intranasally with $2 \times 10^5$ chlamydial EBs per ml. The inventors have confirmed the work of Yang and colleagues (15) in which intranasal inoculation of chlamydial EBs results in systemic dissemination and, in particular, causes infection of the spleen. The inventors have discovered that this systemic dissemination also results in the presence of EBs in the blood of the mice. Therefore, infectivity can be measured by blood culture or by serum/whole blood PCR for chlamydial DNA. Systemic infection is also confirmed and monitored by the presence of elevated IgM and IgG antibody titers. After the systemic murine infection has been established, antimicrobial agents are given to the mice. This is most easily done by adding the antibiotics to the drinking water. The effect of antichlamydial therapy is monitored by serum/whole blood PCR. When the serum/PCR assay suggests eradication of chlamydiae from the bloodstream, the mice are sacrificed and PCR for chlamydial DNA is done on lung, heart, liver, and spleen homogenates. This method is unique because it measures the complete eradication of all life forms of chlamydiae in known murine target organs for chlamydial infection. This in vivo susceptibility method has revealed, for example, that antimicrobial therapy with the triple agents, INH, metronidazole and penicillamine, can completely eradicate *C. pneumoniae* from infected mice in four months. Moreover, following complete eradication of chlamydiae, multiple attempts to reinfect these cured mice via intranasal inoculation have proven unsuccessful. This suggests that effective therapy and complete eradiaction results in the development of protective immunity, and that effective therapy is therefore a way to create effective immunity.

Performing PCR for chlamydial DNA on homogenates of other organ systems can be used to determine the effectiveness of particular antibiotic combinations in eradicating chlamydial infection in those organ systems. Establishment of prior chlamydial infection of those systems can be done by either biopsy or antibody-enhanced radiological imaging. Alternatively, prior infection can be determined statistically by performing PCR for chlamydial DNA on homogenates of the same organ systems in a similarly inoculated but untreated control population. Organ-specific susceptibility is determined by comparing rates of positive PCR assays in the control and treated populations.

An alternative or complementary method of determining the presence of cryptic chlamydial infections in an animal or cell culture is to expose the culture to chlamydia-stimulating compounds. Such compounds include (but are not limited to) cycloheximide, corticosteriods (such as prednisone) and other compounds which are known to stimulate reactivation of cryptic intracellular infections, and disulfide reducing agents (such as dithiotreitol) and other chemicals which cause EBs to turn into RBs. Once the cryptic forms have entered a more active phase, they can be detected using standard detection techniques such as visual detection of inclusion bodies, immunochemical detection of chlamydial antigen, or reverse transcriptase-PCR.

Although the foregoing description is directed toward Chlamydia, it is merely for exemplary purposes and is not intended to limit the invention thereto. The invention therefore is relevant for other to obligate intracellular pathogens. For example, pathogens that must be in an intracellular location in order to replicate, include but are not limited to prions, viruses, Chlamydiae spp., Mycoplasma spp., Ehrilichia spp., Rickettsia spp., Bartinella spp., Borrelia spp., Toxoplasma gondii, Leishmania spp. and Trypanosomes (e.g., Malaria). Additionally, included are pathogens that are able to survive in an intracellular location and can find a physiologic advantage to do so, for example, Legionella spp., Salmonella spp., Listeria spp., Histoplasma spp., Yersinia spp. and Mycobacteria spp. Intracellular pathogens that are able to utilize selective intracellular locations to enhance survivability and/or pathogenics, are embraced in this invention and include but are not limited to Neisseria spp., Staphylococcus spp., Hemophilus spp., *Escherichia coli*, Candida spp. and Torulopsis spp.

REFERENCES

1. Stratton C W. Susceptibility testing revisited. In:: Progress in Clinical Pathology, Volume IX, pages 65–100. Stefanini, M., Gorstein, F., Fink, L. M. (eds), Grune and Stratton, Incorporated, Orlando, Fla., (1983).
2. Stratton C W. The clinical relevance of in vitro tests used as guidelines for antimicrobial therapy. In:: *Antibiotics in Laboratory Medicine*, pp. 849–879. Third Edition. Lorian, V. (ed), The Williams & Wilkins Company, Baltimore, Md., (1991).
3. Hammerschlag M R. *Antimicrobial Agents and Chemotherapy*, 38: 1873–1878 (1994).
4. Gump D W. Antimicrobial susceptibility testing for some atypical microorganisms: chlamydiae, mycoplasmas, Rickettsia, and spirochetes. pp 212–229 In: *Antibiotics in Laboratory Medicine—Fourth Edition*. Lorian V (ed). Williams & Wilkins, Baltimore, (1996).
5. Ehret J M and Judsen F N., *Antimicrobial Agents and Chemotherapy*, 32: 1295–1299 (1988).
6. Gordon F B and Quan A L., *Antimicrobial Agents and Chemotherapy*, 2: 242–244 (1972).
7. Ridgeway G L, et al., *Journal of Antimicrobial Chemotherapy*, 2:71–76 (1976).
8. Blackman H J, et al., *Antimicrobial Agents and Chemotherapy*, 12:673–677 (1977).
9. Rota, T R., *Archives of Andrology*, 4: 63–69 (1980).
10. Kuo C-C and Grayston J. T., *Antimicrobial Agents and Chemotherapy*, 32:257–258 (1988).
11. Yang Z P, et al., *Infection and Immunity*, 39:655–658 (1983).
12. Yang Z P, et al., *Infection and Immunity*, 61:2037–2040 (1993).
13. Kaukoranta-Tolvanen S S, et al., *Microbial Pathogenesis*, 15:293–302 (1993).
14. Yang Z P, et al., *The Journal of Infectious Diseases*, 170:64–467 (1994).
15. Yang Z, et al., *The Journal of Infectious Diseases*, 171:736–738 (1995).
16. Malinverni R. et al., *The Journal of Infectious Diseases*, 172:593–594 (1995).
17. Masson N D, et al., *Antimicrobial Agents and Chemotherapy*, 39:1959–1964 (1995).
18. Moazed T C, et al., *The Journal of Infectious Diseases*, 175:883–890 (1997).
19. Chirgwin K, et al., *The Journal of Antimicrobial Agents and Chemotherapy*, 33:1634–1635 (1989).
20. Fenelon L E, et al., *Journal of Antimicrobial Chemotherapy*, 26:763–767 (1990).
21. Cooper M A, et al., *Journal of Antimicrobial Chemotherapy* 28:407–413 (1991).
22. Wyrick P B, et al., *Clinical Infectious Diseases*, 19: 931–936 (1994).
23. Grassi G G., In: *Chlamydia pneumoniae Infection*. Allegra L, Blasi F (eds), Springer-Verlag, Berlin, pp 23–30 (1995).
24. Khan M A, et al., *Journal of Antimicrobial Agents and Chemotherapy*, 37: 677–685 (1996).
25. Gerding D N, et al., In: *Antibiotics in Laboratory Medicine—Fourth Edition*. Lorian V (ed). Williams & Wilkins, Baltimore, p 879 (1996).
26. Kimura M, et al., *Antimicrobial Agents and Chemotherapy*, 37;801–803 (1993).
27. Niki Y, et al., *Antimicrobial Agents and Chemotherapy*, 38:2296–2299 (1994).
28. Beatty W L, et al., *Microbiology Reviews*, 58:686–699 (1994).
29. Beatty W L, et al., *Trends in Microbiology*, 2:94–98 (1994).
30. Beatty W L, et al., *Proceedings of the National Academy of Science, USA*, 90:3998–4002 (1993).
31. Moulder J W, et al., *Infection and Immununity*, 20:874–883 (1980).
32. Perez-Marines J A, and Storz J., *Infection and Immunity*, 50:453–458 (1985).
33. Meyer K F, and Eddie B., *Proceedings of the Society of Experimental Biology and Medicine*, 30:483–488 (1933).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method for determining susceptibility of Chlamydia to a test agent, said method comprising the steps of:
    a) contacting said Chlamydia in cell or animal culture to the test agent in the absence of cycloheximide; and
    b) determining the presence or absence of chlamydial DNA in the culture, wherein the absence of chlamydial DNA in the culture indicates that said Chlamydia is susceptible to said test agent.

2. The method of claim 1 wherein the test agent is a single agent or plurality of agents.

3. The method of claim 1 wherein the Chlamydia is Chlamydia pneumoniae.

4. The method of claim 3 wherein the DNA encodes MOMP.

5. The method of claim 3 wherein the presence or absence of the DNA is determined by a nucleic acid amplification technique.

6. The method of claim 5 wherein the nucleic acid amplification technique is PCR.

7. An assay for identifying an agent which is capable of inhibiting or eliminating a chlamydial infection, said assay comprising the steps of:

a) preparing tissue culture cells infected with Chlamydia in the absence of cycloheximide;

b) allowing the Chlamydia to replicate in said cells;

c) contacting said cells of step b) with a test agent;

d) isolating DNA from the cells of step c);

e) amplifying the DNA by a nucleic acid amplification technique; and f) determining the presence or absence of amplified DNA, wherein the absence of amplified DNA is indicative that the agent is capable of inhibiting or eliminating a chlamydial infection.

8. The assay of claim 7 wherein the Chlamydia is *Chlamydia pneumoniae.*

9. The assay of claim 7 wherein the amplification technique is PCR.

10. A method of identifying a cell infected with Chlamydia, said method comprising the steps of:

a) treating cultured cells with a disulfide reducing agent to specifically uncoat elementary body phase Chlamydia and release DNA therefrom;

b) subjecting said cells of step a) to protease digestion;

c) amplifying chlamydial DNA in said cells of step b) if present, wherein said amplifying is under conditions that incorporate a tag that specifically binds to a reporter molecule enzyme;

d) exposing the cells of step c) to said reporter molecule enzyme;

e) exposing the cells of step d) to a substrate for the reporter enzyme wherein said reporter enzyme converts said substrate into a reacted substrate; and f) determining the presence of said reacted substrate in said cells of step e), wherein the presence of said reacted substrate in a cell identifies said cell as being infected with Chlamydia.

11. The method of claim 10 wherein the Chlamydia is *Chlamydia pneumoniae.*

12. An assay for identifying an agent which eradicates Chlamydia, said assay comprising the steps of:

a) treating cultured cells grown in the absence of cycloheximide and infected with Chlamydia with a disulfide reducing agent;

b) allowing the Chlamydia to replicate in said cells;

c) contacting said cells of step b) with a test agent;

d) subjecting said cells of step c) to protease digestion;

e) amplifying chlamydial DNA in said cells of step d) if present, wherein said amplifyng is under conditions that incorporate a tag that specifically binds to a reporter molecule enzyme;

f) exposing the cells of step e) to said reporter molecule enzyme;

g) exposing the cells of step f) to a substrate for the reporter enzyme, wherein said reporter enzyme converts said substrate into a reacted substrate; and h) determining the presence of said reacted substrate, wherein the absence of said reacted substrate is indicative that the agent eradicates Chlamydia.

13. A method for determining the presence of Chlamydia, comprising exposing cells to a reducing agent to specifically uncoat elementary body phase Chlamydia and release DNA therefrom; subjecting said cells to protease digestion; and determining the presence or absence of chlamydial DNA, wherein the presence of chlamydial DNA indicates the presence of Chlamydia.

14. The method of claim 13 wherein the Chlamydia is *Chlamydia pneumoniae.*

15. The method of claim 14 wherein the DNA encodes MOMP.

16. The method of claim 13 wherein the presence or absence of chlamydial DNA is determined by a nucleic acid amplification technique.

17. The method of claim 16 wherein the nucleic acid amplification technique is PCR.

* * * * *

UNITED STATES PATENT AND TRADEMARK OFFICE
CERTIFICATE OF CORRECTION

PATENT NO.   : 6,258,532 B1
DATED        : July 10, 2001
INVENTOR(S)  : Charles W. Stratton and William M. Mitchell It is certified that error appears in the above-identified patent and that said Letters Patent is hereby corrected as shown below:

Title page,
U.S. PATENT DOCUMENTS, first patent listed, please change "Linn et al." to
-- Lin Song-Ling et al. --;
U.S. PATENT DOCUMENTS, please add
-- 5,637,687    6/1997    Wiggins …. 536/25.4 --;
OTHER PUBLICATIONS, Drancourt reference, please change "(199f3)" to -- (1993) --;
OTHER PUBLICATIONS, Lay-Schmitt reference, please change "in subgroup" to
-- in a subgroup --;
OTHER PUBLICATIONS, Orfila reference, please change "Chlamydia Trachmatis to
-- Chlamydia Trachomatis --;

Column 3,
Line 10, change "susceptabilty test" to -- susceptability test --;
Line 45, change "metabolsim" to -- metabolism --;

Column 4,
Line 14, change "of at least one test agents" to -- of at least one test agent --;
Line 19, change "antimalarial agent" to -- antimalarial agents --;

Column 8,
Line 35, change "complete eradiaction" to -- complete eradication --;
Line 66, change "other to obligate" to -- other obligate --;

Column 10,
Line 34, change "Infection and Immununity" to -- Infection and Immunity --;

UNITED STATES PATENT AND TRADEMARK OFFICE
CERTIFICATE OF CORRECTION

PATENT NO.   : 6,258,532 B1
DATED        : July 10, 2001
INVENTOR(S)  : Charles W. Stratton and William M. Mitchell It is certified that error appears in the above-identified patent and that said Letters Patent is hereby corrected as shown below:

<u>Column 12,</u>
Line 36, step (e), change "amplifyng" to -- amplifying --

Signed and Sealed this

Eighth Day of October, 2002

Attest:

Attesting Officer

JAMES E. ROGAN
*Director of the United States Patent and Trademark Office*

SEQUENCE LISTING

```
<160> NUMBER OF SEQ ID NOS:   2

<210> SEQ ID NO 1
<211> LENGTH: 38
<212> TYPE: DNA
<213> ORGANISM: Chlamydia pneumoniae

<400> SEQUENCE: 1
```

```
atgaaaaaac tcttaaagtc ggcgttatta tccgccgc                                    38

<210> SEQ ID NO 2
<211> LENGTH: 40
<212> TYPE: DNA
<213> ORGANISM: Chlamydia pneumoniae

<400> SEQUENCE: 2
ttagaatctg aactgaccag atacgtgagc agctctctcg                                  40
```